United States Patent [19]

Furlenmeier et al.

[11] E Re. 29,003

[45] Reissued Oct. 12, 1976

[54] (R)-1-(2-FUROYLOXY)-3-METHYLBUTYL-PENICILLIN

[75] Inventors: André Furlenmeier, Basel; Paul Lanz, Muttenz; Peter Quitt, Fullinsdorf, all of Switzerland; Karl Vogler, deceased, late of Riehen, Switzerland; by Heinrich Vogler, heir at Law, Basel; by Niklaus Eduard Vogler, heir at Law, Riehen, both of Switzerland; by Franziska Elisabeth Vogler, heir at Law, Bochum-Stiepel, Germany

[73] Assignee: Hoffmann-La Roche Inc., Nutley, N.J.

[22] Filed: Oct. 2, 1975

[21] Appl. No.: 619,128

Related U.S. Patent Documents

Reissue of:

[64] Patent No.: 3,839,322
Issued: Oct. 1, 1974
Appl. No.: 215,187
Filed: Jan. 3, 1972

[30] Foreign Application Priority Data

Jan. 20, 1971 Switzerland ..... 848/71

[52] U.S. Cl. ..... 260/239.1
[51] Int. Cl.[2] ..... C07D 99/16
[58] Field of Search ..... 260/239.1

[56] References Cited

FOREIGN PATENTS OR APPLICATIONS 1,125,557 8/1968 United Kingdom ..... 260/239.1

OTHER PUBLICATIONS

Neal et al., Chemical Abstracts, 70:4105(f) (1969).
Peterson et al., Chemical Abstracts, 73:86326(c).

*Primary Examiner*—Gerald A. Schwartz
*Attorney, Agent, or Firm*—Samuel L. Welt; Bernard S. Leon; R. Hain Swope

[57] ABSTRACT

Compounds represented by the following formula

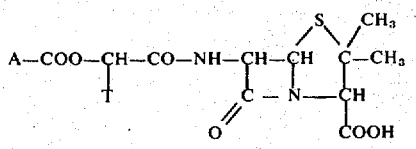

wherein A is a substituted or unsubstituted heterocyclic radical and T is a $C_2$–$C_5$ alkyl, alkenyl, cyclopropylmethyl, cyclobutylmethyl or cyclopentyl group a process for their preparation and novel intermediates therefor are disclosed. These compounds are useful antibiotics.

2 Claims, No Drawings

(R)-1-(2-FUROYLOXY)-3-METHYLBUTYL-PENICILLIN

Matter enclosed in heavy brackets [ ] appears in the original patent but forms no part of this reissue specification; matter printed in italics indicates the additions made by reissue.

DETAILED DESCRIPTION OF THE INVENTION

The present invention is directed to novel 6-acylaminopenicillanic acid compounds represented by the general formula

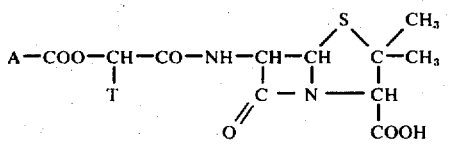

I wherein A is furyl, tetrahydrofuryl, pyrrolyl, pyrrolidinyl, thienyl, oxazolyl, isoxazolyl, thiozolyl, 1,2,3-thiadiazolyl, pyridyl, imidazolyl, pyrazolyl, 1-oxido-pyridyl, tetrahydropyranyl, pyrimidinyl, pyrazinyl, benzofuranyl, indolyl, quniolyl or isoquinolyl which may be substituted with halogen, oxo, hydroxy, $C_1$–$C_3$ alkyl, $C_1$–$C_3$ alkoxy, $C_1$–$C_3$ alkoxy carbonyl or $C_1$–$C_3$ alkanoyl-amino and T is a $C_2$–$C_5$ alkyl, a $C_2$–$C_5$ alkenyl, cyclopropylmethyl, cyclobutyl-methyl or cyclopentyl and pharmaceutically acceptable salts and hydrated forms thereof.

The invention is also directed to the preparation of the compounds of formula I utilizing the novel intermediate compounds represented by the formula

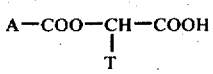

II wherein A and T have the meaning given above, and their functional derivatives.

In accordance with the present invention, the term "halogen" represents all the halogens with fluorine, bromine and chlorine being preferred. Alkyls or alkenyls represented by T in formulas I and II may be straight- or branched-chain. Examples of such substituents include ethyl, n-propyl, isobutyl, n-pentyl, 3-methylbutyl, neopentyl, vinyl, allyl, methyallyl, butenyl and pentenyl. The $C_1$ to $C_3$ alkyl, alkoxy, alkoxycarbonyl and alkanoylamino groups referred to herein are those wherein the alkyl moiety contains from one to three carbon atoms.

Preferred 6-aminopenicillanic acid compounds in accordance with the invention are those wherein A in the above formulas is 3-pyridyl, 2-methyl-4-pyridyl, 3-isoxazolyl, 4-oxazolyl, 2-oxo-2-pyrrolidinyl, pyrazinyl, tetrahydro-2-furyl, 2-acetamido-4-thiazolyl, 1,5-dimethyl-3-pyrazolyl, tetrahydro-4-pyranyl, 1,2,3-thiadiazol-4-yl, 2-furyl or 4-pyridyl. The preferred compounds according to the invention are those wherein T is an alkyl or alkenyl group containing four or five carbon atoms. An especially preferred group of compounds in accordance with the invention are set forth in Table below. Preferred among this group is the compound represented by formula I wherein A is 2-furyl and T is 2-methylpropyl, i.e., [1-(2-furoyloxy)-3-methylbutyl)]-penicillin, especially the R-form thereof. In the Table, the antimicrobial activity of the compounds tested is expressed in terms of the minimal inhibitory concentration in μg./ml. The minimal inhibitory concentration was determined by double dilution series in nutrient bouillon. The activity of the compounds is further demonstrated in vivo by establishing an oral $CD_{50}$ in the mouse against S. aureous and E. coli.

TABLE

| Compound | Minimum Inhibitory Concentration [mg/ml] | | $CD_{50}$ per os in The Mouse [mg/kg] | |
|---|---|---|---|---|
| | S. aureous FDA | E. coli 1346 | S. aureous (Schoch) | E. coli 1346 |
| [(R)-1-(2-furoyloxy-3-methyl-butyl]penicillin sodium | 0.073 | 73 | 0.7 | 16 |
| [(R)-1-(isoniconacyloxy)-3-methyl butyl]penicillin sodium | 0.156 | 19 | 1.1 | 18 |
| (R)-3-methyl-1-[(S)-pyroglutamoyloxy-butyl]penicillin sodium | 0.312 | 0.625 | 2.0 | 37 |
| [(R)-3-methyl-1-[(1,2,3-thiadiazol-4-ylcarbonyl)oxy]-butyl]penicillin sodium | 0.312 | 10 | 7.2 | 93 |
| [(R)-3-methyl-1-{[tetrahydropyran-4-yl)carbonyl]oxy}butyl]penicillin sodium | 1.25 | 19 | 3.1 | 27 |
| [(R)-1-{[(1.5-dimethylpyrazol-3-yl)-carbonyl]oxy}-3-methylbutyl]penicillin sodium | 0.625 | 78 | 2.9 | 42 |
| [(R)-1-{[(2-acetamide-4-thiazolyl)-carbonyl]oxy}-3-methylbutyl]penicillin sodium | 1.25 | 10.0 | 2.4 | 47 |
| [(R)-3-methyl-1-[(RS)-tetrahydro-2-furoyloxy]butyl]-penicillin sodium | 1.25 | 10.0 | 1.6 | 55 |

In accordance with the present invention, the compounds represented by formula I are prepared by condensing 6-amino-penicillanic acid, the carboxyl group of which is in a protected form, with the novel compounds represented by formula II or a functional derivative thereof. Such functional derivatives are conventional and include, for example, halides, azides, anhydrides — particularly mixed anhydrides with strong acids — reactive esters such as the N-hydroxysuccinimide esters, amides, such as imidazolides and the like. After the reaction is completed, the protecting group is cleaved off and, if desired, the product is converted into a salt.

Examples of methods whereby the carboxyl of 6-amino-penicillanic acid can be protected include conversion into a readily cleavable ester such as, for example, the benzyl ester, a p-bromophenacyl ester or a silyl ester such as the trimethyl silyl ester, or by salt formation with an inorganic or tertiary organic base such as, for example, triethylamine. When the condensation of 6-aminopenicillanic acid and the compound represented by formula II is completed, the ester protecting group can be easily removed by methods known in the art. For example, a benzyl ester can be easily removed by catalytic hydrogenation such as, for example, in the presence of a noble metal catalyst such as palladium-on-carbon, and a silyl ester can be cleaved by treating the product with water. Where the carboxyl group of 6-aminopenicillanic acid is protected by salt formation, e.g., with triethylamine, the protecting group can be cleaved by treatment with acids such as, for example, hydrochloric acid, sulfuric acid, phosphoric acid, citric acid and the like at low temperatures, e.g., 0°–5° C.

The condensation of 6-aminopenicillanic acid, having a protected carboxyl group and the compound represented by formula II is carried out by methods well known in the art of peptide chemistry. Thus, for example, the condensation is effected in the presence of a carbodiimide such as, for dicyclohexylcarbodiimide or an oxazolium salt such as, for example, N-ethyl-5-phenyl-isoxazolium-3′-sulfonate, in an inert solvent. Suitable solvents include, for example, ethyl acetate, acetonitrile, dioxan, chloroform, methylene chloride, benzene, dimethylformamide and the like. In a like manner, a salt of 6-aminopenicillanic acid such as, for example, a trialkylammonium salt, is condensed with a reactive functional derivative of a compound represented by formula II. The reaction of 6-aminopenicillanic acid having a protected carboxyl group and an acid compound represented by formula II, or a reactive functional derivative thereof, can conveniently be carried out at a temperature between about −40° C. and 5° C., preferably at about 0° C.

The novel acid starting compounds represented by formula II may be utilized as racemates or in an optically pure form. It is preferred to use the R-enantiomers in the practice of the invention. Specifically, the R configuration referred to pertains to the asymmetrical carbon atom marked with an asterisk in formula IIa.

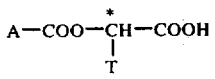

IIa wherein A and T have the meaning given. The acid compounds represented by formula II may be prepared by converting a compound represented by the general formula

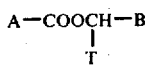

III wherein A and T have the meaning given earlier and B represents a protected carboxyl group, into the free acid form by cleaving the protecting group. The protected carboxyl group represented by B in the above formula may be a readily cleavable ester group such as, for example, the benzyl or tert. butyl ester groups. The conversion of the protected carboxyl group into the free acid is readily effected in the case of the benzyl ester, for example, by catalytic hydrogenation in the presence of a noble metal catalyst. Where the protecting group is the tert. butyl ester, cleavage may be accomplished by treatment with acid such as, for example, a mineral acid-hydrochloric acid- or trifluoroacetic acid and the like. The subsequent conversion of the acid compounds represented by formula II, if desired, into reactive functional derivatives thereof such as, for example, halides, azides, anhydrides, esters, amides and the like may be carried out by methods recognized in the art as being conventional.

The compounds represented by formula III above may be obtained by conventional means such as, for example, utilizing known means such as described herein to protect the carboxyl group in a compound represented by the general formula

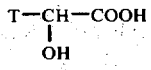

IV wherein T has the meaning given earlier, and reacting the resulting product with a compound represented by the general formula

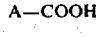

wherein A has the meaning given earlier, for example, in the presence of benzenesulfonyl chloride.

The 6-acyl derivatives of 6-aminopenicillanic acid provided by the present invention possess a broad spectrum of activity against gram-positive microorganisms such as Staphylococcus aureus, Diplococcus pneumoniae and Streptococcus pyogenes and gram-negative microorganisms such as Escherichia coli, Proteus vulgaris, Proteus mirabilis and Salmonella typhi murium. Their antibiotic and bactericidal activity allows them to be utilized therapeutically and as disinfectants. It is preferred in accordance with the invention to administer the novel penicillin compounds described herein orally in view of their superior stability against gastric acid. It is contemplated, in the case of adults, that oral dosage forms each containing 200–600 mg. of active penicillin compound are administered three or four times daily. This dosage regimen may be adjusted by the clinician as the therapeutic situation requires. The novel penicillin compounds of the invention may also be administered parenterally, rectally or topically in suitable dosage forms and may be administered in the form of their pharmaceutically acceptable salts or hydrates.

Examples of the pharmaceutically acceptable salts of the penicillin compounds represented by formula I include salts with inorganic bases such as, for example, the alkali metal salts, e.g., the sodium or potassium salt; ammonium salts; alkaline earth metal salts e.g., the calcium salt and the like; and salts with organic bases such as amine compounds, for example, N-ethyl piperidine, procaine, dibenzylamine, N,N′-dibenzylethylethylenediamine, alkylamines, dialkylamines or the like. The foregoing salts can also be hydrated. The hydration can be effected during the manufacturing process or can occur gradually as a consequence of the hygroscopic properties of an initially anhydrous salt.

The compounds represented by formula I and their salts can exist as optically pure isomers and as diastereomer mixtures. The preferred compounds in accordance with the invention are those wherein the acyl group substituted on the amine group at position 6 of 6-aminopenicillanic acid has the R configuration. Specifically, the R configuration referred to pertains to the asymmetrical carbon atom marked with an asterisk in the following formula

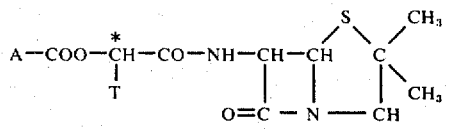

wherein A and T have the meanings given above.

For purposes of administration, the novel 6-acyl derivatives of 6-aminopenicillanic acid of the present invention can be combined with conventional compatible organic or inorganic pharmaceutical carrier materials known in the art. Such materials include, for example, water, gelatin, gums, lactose, starches, magnesium stearate, talc, vegetable oils, polyalkylene glycols, petroleum jelly and the like. Such pharmaceutical preparations may be in unit dosage form and may additionally contain other therapeutically valuable substances or conventional pharmaceutical adjuvants such as preservatives, stabilizing agents, wetting agents, emulsifying agents, buffers and the like. The pharmaceutical preparations can be in conventional solid dosage forms such as tablets, capsules, dragees and the like, conventional semi-solid forms such as ointments and creams, conventional liquid forms such as solutions, suspensions, emulsions and the like and other conventional dosage forms such as dry ampules, suppositories and the like. Such preparations may be submitted to conventional pharmaceutical expedients such as, for example, sterilization and the like.

The following Examples illustrate the process provided by the invention. All temperatures are in degrees Centigrade.

EXAMPLE 1

[(R)-1-(2-furoyloxy)-3-methylbutyl]penicillin sodium 264.0 g. of (R)-2-hydoxy-isocaproic acid were dissolved in 1.8 liters of absolute dioxan in a three-necked flask fitted with a stirrer, thermometer and reflux condenser with a calcium chloride tube. The solution was treated successively with 285 ml. of triethylamine and 236 ml. of benzyl chloride and heated at an internal temperature of 100° for 20 hours with stirring in an oil-bath. After cooling, the resulting triethylamine hydrochloride was filtered off and washed with 500 ml. of ethyl acetate. The filtrate was evaporated under reduced pressure at 50°. The residual oil was dissolved in 800 ml. of ethyl acetate and washed twice with 150 ml. portions of 3-N hydrochloric acid, twice with 100 ml. portions of 5 percent sodium chloride solution, twice with 150 ml. portions of 10 percent potassium bicarbonate solution and twice with 100 ml. portions of 5 percent sodium chloride solution. After each of these washings, the oil was rinsed with 200 ml. of ethyl acetate. The ethyl acetate solutions were dried over magnesium sulphate and evaporated under reduced pressure at 50°. The crude product which was thus-obtained was distilled at 0.3 Torr (112°–115°). There was obtained benzyl-(R)-2-hydroxy-isocaproate; $[\alpha]_D^{25} = +18.0°$ (c = 1 in methanol); $n_D^{23} = 1.498$.

27 Ml. of benzenesulphonyl chloride were added dropwise at 25° with stirring over a period of 20 minutes to a solution of 23.6 g. of furan-2-caboxylic acid in 100 ml. of pyridine. The mixture was then stirred for 30 minutes at 25°. A total of 44.4 g. of benzyl-(R)-2-hydroxy-isocaproate were then added dropwise with stirring. The solution was warmed to 60° for 2 hours.

The pyridine was then distilled off under reduced pressure at 30°–50° and the residue dissolved in 600 ml. of 3-N hydrochloric acid with the addition of ice and extracted twice with 250 ml. portions of ethyl acetate. The ethyl acetate solutions were washed once with 100 ml. of 3-N hydrochloric acid, twice with 100 ml. portions of water, twice with 100 ml. portions of 5 percent sodium bicarbonate solution and twice with 100 ml. portions of water and dried with magnesium sulphate. The ethyl acetate was distilled off under reduced pressure at 40° and the oil dried for 60 minutes under reduced pressure at 60°. There was thus obtained benzyl-(R)-2-(2-furoyloxy)-isocaproate; $[\alpha]_D^{25} = +9.0°$ (c = 4.0 in alcohol).

A total of 55.5 g. of benzyl-(R)-2-(2-furoyloxy)-isocaproate were hydrogenated in 400 ml. of alcohol after the addition of 5 g. of palladium-on-charcoal (5 percent) until the theoretical amount of hydrogen had been taken up. The catalyst was filtered off by suction and the filtrate evaporated under reduced pressure at 40°. The oil thus obtained was dissolved in 250 ml. of 8 percent sodium bicarbonate solution and the resulting solution washed twice with 80 ml. portions of ether. The pH of the bicarbonate solution was adjusted to pH 2 with concentrated hydrochloric acid and extracted three times with 100 ml. portions of ethyl acetate. The ethyl acetate solutions were washed twice with 50 ml. portions of water, dried with magnesium sulphate and evaporated under reduced pressure at 45°. The residual oil was dried for 2 hours at 0.4 Torr and 40° to give (R)-2-(2-furoyloxy)-isocaproic acid; $[\alpha]_D^{25} = +7.0$ (c = 4.0 in alcohol).

A mixture of 22.6 g. of the R-2-(2-furoyloxy)-isocaproic acid thus obtained, 80 ml. of absolute benzene and 36 ml. of thionyl chloride was warmed for 2.5 hours, evaporated and dried. There was thus obtained 24.5 g. of R-α-(2-furoyloxy)-isocaproic acid chloride. This was dissolved in 70 ml. of methylene chloride and the solution added dropwise at 0° with stirring to a solution of 21.6 g. of 6-aminopenicillanic acid in a mixture of 150 ml. of methylene chloride and 23 ml. of triethylamine. The reaction mixture was kept for 20 hours at 0° and then evaporated under reduced pressure at 20°. The residue was dissolved in 150 ml. of ice-water and extracted twice with 50 ml. portions of ether. The pH of the aqueous phase was adjusted to pH 2 at 0° with 3-N sulphuric acid and extracted three times with 80 ml. portions of ethyl acetate. The ethyl acetate solutions were collected and washed three times with 20 ml. portions of ice-cold 5 percent sodium chloride solution, dried with magnesium sulphate and evaporated under reduced pressure at 20°. The residue was dissolved in 300 ml. of absolute ether, the solution filtered and treated with stirring with 50 ml. of 2-M sodium 2-ethylcaproate solution in ethyl acetate. The [(R)-1-(2-furoyloxy)-3-methylbutyl]penicillin sodium which precipitated was filtered off by suction, washed with absolute ether and low-boiling petroleum ether and, after drying, recrystallized from water-isopropanol to yield a product of melting point 182°–183° (with decomposition); $[\alpha]_D^{25} = +221.5°$ (c = 2.0 in water).

EXAMPLE 2

[(R)-1-(isonicotinoyloxy)-3-methylbutyl]penicillin sodium (R)-2-(isonicotinoyloxy)-isocaproic acid, melting point 138°–139°; $[\alpha]_D^{25} = 22.3°$ (c = 3 in ethanol), was prepared via its benzyl ester in a manner analogous to that described for the preparation of the starting material in Example 1.

A mixture of 23.7 g. of (R)-2-(isonicotinoyloxy)-isocaproic acid thus formed, 80 ml. of absolute benzene and 36 ml. of thionyl chloride was warmed for 2 hours, evaporated and thereafter evaporated three times under reduced pressure at 45° with 30 ml. portions of absolute benzene and dried. There was obtained 25.6 g. of (R)-α-(isonicotinoyloxy)-isocaproic acid chloride hydrochloride. This was dissolved in 80 ml. of chloroform and added dropwise at 0° with stirring to a solution of 21.6 g. of 6-aminopenicillanic acid in a mixture of 150 ml. of chloroform and 42 ml. of triethylamine. The reaction mixture was kept for 20 hours at 0° and then evaporated under reduced pressure at 20°. The residue was dissolved in 200 ml. of ice-water and extracted twice with 70 ml. portions of ethyl acetate. The pH of the aqueous phase was adjusted to pH 2.5 at 0° with citric acid and extracted three times with 100 ml. portions of ethyl acetate. The ethyl acetate solutions were collected and washed three times with 30 ml. portions of ice-cold 5 percent sodium chloride solution, dried with magnesium sulphate and evaporated under reduced pressure at 20°. The residue was dissolved in 100 ml. of ethyl acetate and the solution treated with stirring with 50 ml. of 2-M sodium-2-ethylcaproate solution in ethyl acetate and with 200 ml. of absolute ether. The [(R)-1-(isonicotinoyloxy)-3-methylbutyl]penicillin sodium which precipitated was filtered off by suction, washed with absolute ether and low-boiling petroleum ether and, after drying, recrystallized from water/isopropanol to yield a product of melting point 197°–198° (with decomposition); $[\alpha]_D^{25} = +227°$ (c = 1.0 in water).

EXAMPLE 3

(R)-3-methyl-1-[(S)pyroglutamoyloxybutyl]penicillin sodium

A total of 14.2 g. of (S)-pyroglutamic acid were suspended in 60 ml. of dimethylformamide and brought into solution with 15.4 ml. of triethylamine. There was then added at −60° with stirring over 20 minutes 52 ml. of a 5.2 molar solution of phosgene in toluene and, after a further 5 minutes, with strong stirring, a solution of 22.2 g. of benzyl-(R)-2-hydroxyisocaproate in 80 ml. of pyridine, which has been previously cooled to from about −40° to −50°. The mixture was then maintained for 16 hours at from 2°–4° and evaporated under reduced pressure with a receiver cooled with dry-ice. The residue was taken up in ether and washed three times each with 1-N hydrochloric acid, water, 10 percent potassium bicarbonate and water, dried over sodium sulphate and evaporated under reduced pressure. The residue which contained benzyl-(R)-2-[(S)-pyroglutamoyloxy]-isocaproate was hydrogenated in glacial acetic acid/water (95:5) with 5 percent palladium-on-charcoal until no more hydrogen was taken up. It was then filtered off from the catalyst and evaporated under reduced pressure. After crystallization of the residue from ethyl acetate/petroleum ether, there was obtained 11 g. of (R)-2-[(S)-pyroglutamoyloxy-isocaproic acid of melting point 148°–150° (after transformation at 80°); $[\alpha]_D^{25} = +20.4°$ (c = 1.0 in methanol).

A total of 9.2 g. of 6-aminopenicillanic acid were stirred at 0° for one hour in 100 ml. of absolute chloroform with 12.0 ml. of triethylamine. Meanwhile, a solution of 10.4 g. of (R)-2-[(S)-pyroglutamoyloxy]-isocaproic acid formed above and 6.0 ml. of triethylamine in 100 ml. of absolute chloroform at −10° chloroform was treated with 5.2 g. of pivaloyl chloride and stirred for 20 minutes at −10°. The mixture was then cooled to −40°, the 6-aminopenicillanic acid solution added and the mixture subsequently maintained for 16 hours at 0°. The solution was then evaporated under reduced pressure at a bath temperature of 20°, taken up in water and extracted twice with ethyl acetate. After washing the ethyl acetate with water and saturated sodium chloride solution and drying it over sodium sulphate, it was concentrated in vacuum at a bath temperature of 20° to 80 ml. and stirred into 800 ml. of petroleum ether. After decantation, this procedure was repeated, chloroform being used in place of ethyl acetate. The decantation residue was taken up in 100 ml. of acetone and treated with 20 ml. of 2-M sodium-2-ethylcaproate in ethyl acetate, precipitated with petroleum ether and decanted. From methanol/isopropyl ether there crystallized (R)-3-methyl-1-[(S)-pyroglutamoyloxybutyl]-penicillin sodium of melting point 180° (with decomposition); $[\alpha]_D^{25} = +187.0°$ (c = 1.0 in water).

EXAMPLE 4

[[(RS)-1-(5-bromo-2-furoyl)oxy]-3-methylbutyl]-penicillin sodium (R)-2-(5-bromo-2-furoyloxy)-isocaproic acid was prepared via its tert. butyl ester in a manner analogous to that described for the preparation of the starting material in Example 14.

In a manner analogous to that described in Example 1, utilizing the (R)-2-(5-bromo-2-furoyloxy)-isocaproic acid thus formed there was obtained [[(RS)-1-(5-bromo-2-furoyl)oxy]-3-methylbutyl]-penicillin sodium of melting point 205°–206° (with decomposition); $[\alpha]_D^{25} = +189°$ (c = 1 in water).

EXAMPLE 5

[[(R)-1-(2,6-dimethoxyisonicotinyl)oxy]-3-methylbutyl]penicillin sodium

In a manner analogous to that described in Example 1, (R)-2-(2,6-dimethoxyisonicotinoyloxy)-isocaproic acid; mp 79°–81° $[\alpha]_D^{25} = +12.2°$ (c = 2 in ether) was prepared via the corresponding benzyl ester. Using this compound as a starting material [[(R)-1-(2,6-dimethoxyisonicotinyl)oxy]-3-methylbutyl] penicillin sodium; mp 170° (with decomposition); $[\alpha]_D^{25} = +157°$ (c = 2 in water) was prepared in accordance with the method of Example 1.

EXAMPLE 6

[(R)-3-methyl-1-[(5-methyl-2-furoyl)oxy]butyl]-penicillin sodium

In a manner analogous to that described in Example 1, (R)-2-(5-methyl-2-furoyloxy)-isocaproic acid was prepared via the corresponding benzyl ester. Using this compound as a starting material [(R)-3-methyl-1-[(5-methyl-2-furoyl)oxy]butyl]penicillin sodium; mp 204° (with decomposition); $[\alpha]_D^{25} = +211.3°$ (c = 1 in water) was prepared in accordance with the method of Example 1.

EXAMPLE 7

[(R)-1-[2-benzofuryloxy]-3-methylbutyl]penicillin sodium

In a manner analogous to that described in Example 1, (R)-2-(2-benzofuroyloxy)-isocaproic acid was prepared via the corresponding benzyl ester. Using this compound as a starting material [(R)-1-[2-benzofuroyloxy]-3-methylbutyl]penicillin sodium; mp 197°; $[\alpha]_D^{25} = +183.3°$ (c = 1 in water) was prepared in accordance with the method of Example 1.

EXAMPLE 8

[(R)-1-[(3-methyl-5-isoxazolyl)-carbonyloxyl]-3-methylbutyl]penicillin sodium

In a manner analogous to that described in Example 1, (R)-2-(3-methyl-5-isoxazolyl-carbonyloxy)-isocaproic acid; mp. 59°–62°; $[\alpha]_D^{25} = +13°$ (c = 2 in ethanol) was prepared via the corresponding benzyl ester. Using this compound as a starting material [(R)-1-[(3-methyl-5-isoxazolyl)-carbonyloxy]-3-methylbutyl]-penicillin sodium mp. 185° (with decomposition), $[\alpha]_D^{25} = +214.3°$ (c = 2 in water) was prepared in accordance with the method of Example 1.

EXAMPLE 9

[(RS)-1-(3-furoyloxy)-3-methylbutyl]penicillin sodium

In a manner analogous to that described in Example 1, (RS)-2-(3-furoyloxy)-isocaproic; mp 85°–87° was prepared via the corresponding benzyl ester. Using this compound as a starting material [(RS)-1-(3-furoyloxy)-3-methylbutyl]penicillin sodium; mp 208° (with decomposition); $[\alpha]_D^{25} = +210.6°$ (c = 0.5 in water) was prepared in accordance with the method of Example 1.

EXAMPLE 10

[(S)-1-(2-furoyloxy)-3-methylbutyl]penicillin sodium

In a manner analogous to that described in Example 1, (S)-2-(2-furoyloxy)-isocaproic acid; $[\alpha]_D^{25} = -7°$ (c = 4 in ethanol) was prepared via the corresponding benzyl ester. Using this compound as a starting material [(S)-1-(2-furoyloxy)-3-methylbutyl]penicillin sodium; mp 150° (with decomposition) $[\alpha]_D^{25} = +216°$ (c = 2 in water) was prepared in accordance with the method of Example 1.

EXAMPLE 11

[(R)-3-methyl-1-{[(1,2,3,6-tetrahydro-2,6-dioxo-4-pyrimidinyl)carbonyl]oxy}butyl]penicillin sodium In a manner analogous to that described in Example 1, (R)-2-[(1,2,3,6-tetrahydro-2,6-dioxo-4-pyrimidinyl)-carbonyloxy]-isocaproic acid; mp 94°–96° $[\alpha]_D^{25} = +15.5°$ (c = 2 in methanol), was prepared via the corresponding benzyl ester. Using this compound as a starting material [(R)-3-methyl-1-{[(1,2,3,6-tetrahydro-2,6-dioxo-4-pyrimidinyl)carbonyl]oxy}butyl]-penicillin sodium; mp from 220° (with decomposition); $[\alpha]_D^{25} = +162.5°$ (c = 1 in water) was prepared in accordance with the method of Example 1.

EXAMPLE 12

[(R)-3-methyl-1-{[(1-methylimidazol-4-yl)carbonyl]-oxy}butyl]penicillin

In a manner analogous to that described in Example 1, (R)-2-(1-methyl-4-imidazolylcarbonyloxy)-isocaproic acid was prepared via the corresponding benzyl ester. Using this compound as a starting material [(R)-3-methyl-1-{[(1-methylimidazol-4-yl)carbonyl]-oxy}-butyl]penicillin; $[\alpha]_D^{25} + = +182.8°$ (c = 1 in ethanol) was prepared in accordance with the method of Example 1.

EXAMPLE 13

[(R)-1-[(4-isoquinolylcarbonyl)oxy]-3-methylbutyl]-penicillin sodium

In a manner analogous to that described in Example 1, (R)-2-(4-isoquinolylcarbonyloxy)-isocaproic acid was prepared via the corresponding benzyl ester. Using this compound as a starting material [(R)-1-[(4-isoquinolylcarbonyl)oxy]-3-methyl-butyl]penicillin sodium; mp 136°; $[\alpha]_D^{25} = +192.7°$ (c = 1 in ethanol) was prepared in accordance with the method of Example 1.

EXAMPLE 14

[(R)-3-methyl-1-[(1,2,3-thiadiazol-4-yl carbonyl)oxy] butyl]penicilin sodium

A total of 13.0 g. of 1,2,3-thiadiazol-4-carboxylic acid was suspended in 100 ml. of pyridine and treated dropwise at 25°–35° over a period of 20 minutes with 12.8 ml. of benzene-sulphonyl chloride. The mixture was stirred at room temperature for an additional 30 minutes to yield a clear solution. 17.9 G. of tert.butyl-(R)-α-hydroxyisovalerate were then added over a period of 20 minutes with further stirring, the temperature rising to ca 40°. After stirring for two hours at 60°, the mixture was evaporated under reduced pressure, suspended in 200 ml. of ethyl acetate and filtered off. The precipitate was washed twice with ethyl acetate and the combined filtrates were washed three times rapidly with ice-cold dilute hydrochloric acid, once with ice-water and three times with 10 percent potassium bicarbonate solution, dried over sodium sulphate and evaporated under reduced pressure. The residue which contained tert. butyl-(R)-2-(1,2,3-thiadiazol-4-yl-carbonyloxy)-isocaproate was irrigated with 100 ml. of trifluoroacetic acid and evaporated after half an hour under reduced pressure, taken up in ether and exhaustively extracted with 10 percent potassium bicarbonate. The combined bicarbonate extracts were acidified to Congo red and extracted three times with ethyl acetate. After washing, drying and evaporation of the solvent, there remained 19 g of a crystallizing oil. Recrystallization from isopropanol yielded 12 g. of (R)-2-(1,2,3-thiadiazol-4-yl-carbonyloxy)-isocaproic acid; melting point 104°–105°; $[\alpha]_D^{25} = +20.0°$ (c = 1 in methanol).

In a manner analogous to that described in Example 1, utilizing the (R)-2-(1,2,3-thiadiazol-4-yl-carbonyloxy)-isocaproic acid thus formed there was obtained [(R)-3-methyl-1-[(1,2,3-thiadiazol-4-yl-carbonyl)oxy]butyl]penicillin sodium; mp 210° (with decomposition); $[\alpha]_D^{25} = +240.2°$ (c = 1 in water).

EXAMPLE 15

[(R)-3-methyl-1-{[(tetrahydropyran-4-yl)carbonyl]-oxy}butyl]penicillin sodium (R)-2-(tetrahydropyran-4-ylcarbonyloxy)-isocaproic acid was prepared via its benzyl ester in a manner analogous to that described for the preparation of the starting material in Example 22.

In a manner analogous to that described in Example 1, utilizing the (R)-2-(tetrahydropyran-4-ylcarbonyloxy)-isocaproic acid formed above there was obtained [(R)-3-methyl-1-{[(tetrahydropyran-4-yl)carbonyl]-oxy}butyl]penicillin sodium; mp 183° (with decomposition); $[\alpha]_D^{25} = 218.5°$ (c = 1 in methanol).

EXAMPLE 16

[(R)-1-{[(1,5-dimethylpyrazol-3-yl)-carbonyl]oxy}-3-methylbutyl penicillin sodium A total of 19.2 g. of 1,5-dimethylpyrazole-3-carboxylic acid was heated at reflux for 20 minutes with 80 ml. of thionyl chloride after which the excess thionyl chloride was removed under reduced pressure. The mixture was evaporated two additional times under reduced pressure with toluene, then taken up in 100 ml. of toluene and added dropwise at 0° with stirring to 22.4 g. of tert. butyl-(R)-α-hydroxyisocaproate in 80 ml. of pyridine. After stirring for two hours at room temperature, the mixture was evaporated under reduced pressure, taken up in ether and washed three times each with water and a 10 percent aqueous solution of potassium bicarbonate. After drying and evaporating off the solvent, there remained 25.5 g. of a residue of melting point 69°–71° which crystallized under petroleum ether. This residue, which contained tert. butyl-(R)-2-(1,4-dimethylpyrazol-3-yl-carbonyloxy)-isocaproate, was left to stand at room temperature for 30 minutes with 50 ml. of trichloroacetic acid and, after evaporation in vacuum, was dissolved in ether and exhaustively extracted with 10 percent potassium bicarbonate. After acidification of the bicarbonate extracts to Congo red, it was extracted with ether and the ether evaporated under reduced pressure after washing and drying. The residue which remained was recrystallized from ethyl acetate to yield 16 g. of (R)-2-(1,5-dimethylpyrazol-3-ylcarbonyloxy)-isocaproic acid; mp 155°–161° $[\alpha]_D^{25} = +13.1°$ (c = 1.0 in methanol).

In a manner analogous to that described in Example 1, utilizing the (R)-2-(1,5-dimethyl-3-pyrazolylcarbonyloxy)-isocaproic acid formed above there was obtained [(R)-1-{[(1,5-dimethylpyrazol-3-yl)-carbonyl]oxy}-3-methylbutyl]penicillin sodium; mp 205° (with decomposition); $[\alpha]_D^{25} = +196.7°$ (c = 1 in water).

EXAMPLE 17

[(R)-1-{[(2-acetamido-4-thiazolyl)-carbonyl]oxy}-3-methylbutyl]penicillin sodium A suspension of 14.4 g. of 2-acetamido-4-thiazolecarboxylic acid in 200 ml. of dimethylformamide was brought into soluton with 11.9 ml. of triethylamine. It was then treated slowly at −60° with strong stirring with 38.1 ml. of a 2.86 molar solution of phosgene in toluene and then a solution of 14.6 g. of tert. butyl-(R)-2-hydroxyisocaproate in 50 ml. of pyridine which has been previously cooled to ca −50°, was added in one portion. After the mixture had reached room temperature, it was evaporated under reduced pressure and the residue taken up in ether and washed three times each with water and a 10 percent aqueous potassium bicarbonate solution, dried and once more evaporated under reduced pressure. There remained 26 g. of a crystalline mass which contained tert. butyl-(R)-2-(2-acetamido-4-thiazolecarbonyloxy)-isocaproate. This mass was allowed to stand for 30 minutes at room temperature with 100 ml. of trifluoroacetic acid. After removal of the solvent under reduced pressure, the residue was taken up in ether and exhaustively extracted with 10 percent potassium bicarbonate solution. After acidification of the aqueous solution to pH 3, it was extracted three times with ethyl acetate and the extract, after washing with water and drying over sodium sulphate, was evaporated under reduced pressure. (R)-2-(2-acetamido-4-thiazolecarbonyloxy)-isocaproic acid remained as a non-crystallizing resin.

In a manner analogous to that described in Example 3, utilizing as a starting material (R)-2-(2-acetamido-4-thiazolyl-carbonyloxy)-isocaproic acid there was obtained [(R)-1-{[2-acetamido-4-thiazolyl)-carbonyl-]oxy}-3-methylbutyl]penicillin sodium; mp 220° (with decomposition); $[\alpha]_D^{25} = +151.5°$ (c = 1 in water).

EXAMPLE 18

[(R)-3-methyl-1-(RS)-tetrahydro-2-furoyloxy]butyl]-penicillin sodium (R)-2-[(RS)-tetrahydro-2-furoyloxy]-isocaproic acid [$[\alpha]_D^{25} = -7°$ (c = 4 in ethanol)] was prepared via its benzyl ester in a manner analogous to that described for the preparation of the starting material in Example 1.

In a manner analogous to that described in Example 1, utilizing as a starting material (R)-2-[(RS)-tetrahydro-2-furoyloxy]-isocaproic acid there was obtained [(R)-3-methyl-1-[(RS)-tetrahydro-2-furoyloxy]butyl]-penicillin sodium; mp 170°–185° (with decomposition); $[\alpha]_D^{25} = +200°$ (c = 1 in water).

EXAMPLE 19

(RS)-1-(2-furoyloxy)-butyl penicillin sodium (RS)-2-(2-furoyloxy)-valeric acid, melting point 53°–56°, was prepared via its benzyl ester in a manner analogous to that described for the preparation of the starting material in Example 35.

In a manner analogous to that described in Example 1, utilizing as a starting material (RS)-2-(2-furoyloxy)-valeric acid there was obtained (RS)-1-(2-furoyloxy)-butyl penicillin sodium; mp 165°–170° (with decomposition); $[\alpha]_D^{25} = +209°$ (c = 1 in water).

EXAMPLE 20

[(RS)-1 [(1,6-dihydo-6-oxonicotinoyl)-oxy]-3-methylbutyl]penicillin sodium (RS)-2-(1,6-dihydo-6-oxonicotinoyloxy)-isocaproic acid, melting point 167°–170°, was prepared via its benzyl ester in a manner analogous to that described for the preparation of the starting material in Example 35.

In a manner analogous to that described in Example 1, utilizing as a starting material (RS)-2-(1,6-dihydro-6-oxonicotinoyloxy)-isocaproic acid there was obtained [(RS)-1-[(1,6-dihydo-6-oxonicotinoyl)-oxy]-3-methylbutyl]penicillin sodium; mp 200° (with decomposition); $[\alpha]_D^{25} = +191°$ (c = 1 in water).

EXAMPLE 21

[(R)-3-methyl-1-[(pyrazinylcarbonyl)oxy]butyl]-penicillin potassium (R)-2-(pyrazinylcarbonyloxy)-isocaproic acid was prepared via its tert. butyl ester in a manner analogous to that described for the preparation of the starting material in Example 17.

In a manner analogous to that described in Example 3, utilizing the thus-formed (R)-2-(pyrazinylcarbonyloxy)-isocaproic acid, there was obtained [(R)-3-methyl-1-[(pyrazinylcarbonyl)oxy]butyl]penicillin potassium; mp 150° (with decomposition); $[\alpha]_D^{25} = +186.5°$ (c = 1 in water).

EXAMPLE 22

[(R)-3-methyl-1-[(1-oxidonicotinoyl)oxy]butyl]-penicillin sodium

A total of 17.8 g of nicotinoyl chloride hydrochloride was dissolved in 150 ml of pyridine and 50 ml of dimethylfromamide and the solution treated slowly with stirring at a temperature not over 15° with 22.2 g of benzyl-(R)-α-hydroxy-isovalerate (prepared from (R)-2-hydroxy-isovaleric acid and benzyl chloride in a manner analogous to that described, for the preparation of the corresponding compound in Example 1). After stirring for 2 hours at room temperature, the mixture was evaporated under reduced pressure. The residue was taken up in ether, washed three times with water and extracted six times with ice-cold 3-N hydrochloric acid. The hydrochloride phases were immediately allowed to run into saturated sodium bicarbonate solution and the base which was thus released was extracted three times with ether. After washing and drying, it was evaporated under reduced pressure and there were obtained 27 g of a resin which contained benzyl-(R)-2-(nicotinoyloxy)-isocaproate. The resin was then hydrogenated in 200 ml. of ethanol with 2 g. of 5 percent palladium-on-charcoal unit 2 equivalents of hydrogen had been taken up. After filtration and evaporation, the residue was taken up in 10 percent potassium bicarbonate, washed twice with ether and adjusted to pH 3 with citric acid. After extraction with ether, washing, drying and evaporation of the extract, there was obtained a crystallizing oil. Recrystallization from ethyl acetate/petroleum ether yielded 14 g of (R)-2-(nicotinoyloxy)-isocaproic acid; mp 101°–103°; $[\alpha]_D^{25} = +18.8°$ (c = 1.0 in methanol).

The N-oxide of the above acid was obtained by dissolving 26.4 g. of it in 70 ml. of glacial acetic acid by treating for three hours at 70°–80° with 11 ml. of 30 percent hydrogen peroxide. After the addition of an additional 8 ml. of 30 percent hydrogen peroxide, the mixture was left overnight at the same temperature. The mixture was then cautiously evaporated under reduced pressure and evaporated off twice with 50 ml. portions of water, care being taken to ensure that the mixture is never evaporated to dryness. This residue was taken up in chloroform, washed four times with water, dried and evaporated under reduced pressure. Recrystallization from ethyl acetate yielded 19 g of (R)-2-nicotinoyloxy-isocaproic acid N-oxide; mp 132°–134°; $[\alpha]_D^{25} = +20.8°$ (c = 1.0 in methanol).

In a manner analogous to that described in Example 1, utilizing the thus-formed (R)-2-(nicotinoyloxy)-isocaproic acid N-oxide there is obtained [(R)-3-methyl-1-[(1-oxidonicotinoyl)oxy]butyl]penicillin sodium; mp 175° (with decomposition); $[\alpha]_D^{25} = +168.3°$ (c = 1 in water).

EXAMPLE 23

[(R)-1-[(4-chloropicolinoyl)oxy]-3-methylbutyl]-penicillin sodium (R)-2-(4-chloropicolinoyloxy)-isocaproic acid (melting point 120°–122°) was prepared via its tert. butyl ester in a manner analogous to that described for the preparation of the starting material in Example 17.

In a manner analogous to that described in Example 3, utilizing the above (R)-2-(4-chloropicolinoyloxy)-isocaproic acid there was obtained [(R)-1-[(4-chloropicolinoyl)oxy]-3-methyl-butyl]penicillin sodium; melting point 140° (with decomposition); $[\alpha]_D^{25} = +146.7°$ (c = 1 in water).

EXAMPLE 24

[(R)-1-[(2,6-dichloroisonicotinoyl)oxy]-3-methylbutyl]penicillin sodium (R)-2-(2,6-dichloroisonicotinoyloxy)-isocaproic acid melting point 79°–81° (with decomposition) was prepared via its tert. butyl ester in a manner analogous to that described for the preparation of the starting material in Example 16.

In a manner analogous to that described in Example 1, utilizing the above (R)-2-(2,6-dichloroisonicotinoyloxy)-isocaproic acid there was obtained [(R)-1-[(2,6-dichloroisonicotinoyl)oxy]-3-methylbutyl]penicillin sodium; mp. from 162° (with decomposition); $[\alpha]_D^{25} = +164.6°$ (c = 2 in water).

EXAMPLE 25

[(R)-1-[(4-oxazolylcarbonyl)oxy]-3-methylbutyl]-penicillin sodium (R)-2-(4-oxazolylcarbonyloxy)-isocaproic acid was prepared via its benzyl ester in a manner analogous to that described for the preparation of the starting material in Example 1.

In a manner analogous to that described in Example 1, utilizing as a starting material (R)-2-(4-oxazolylcarbonyloxy)-isocaproic acid there was obtained [(R)-1-[(4-oxazolylcarbonyl)oxy]-3-methylbutyl]penicillin sodium; mp 173° (with decomposition); $[\alpha]_D^{25} = +150.8°$ (c = 1 in ethanol).

EXAMPLE 26

[(R)-3-methyl-1-[(2-methylisonicotinoyl)oxy]-butyl]-penicillin sodium (R)-2-(2-methylisonicotinoyloxy)-isocaproic acid was prepared via its benzyl ester in a manner analogous to that described for the preparation of the starting material in Example 22.

In a manner analogous to that described in Example 1, utilizing the thus-formed (R)-2-(2-methylisonicotinoyloxy)-isocaproic acid there was obtained [(R)-3-methyl-1-[(2-methyl-isonicotinoyl)oxy]-butyl]penicillin sodium; mp 195°–200° (with decomposition); $[\alpha]_D^{25} = +188°$ (c = 1 in water).

EXAMPLE 27

[(R)-1-[(3-isoxazolylcarbonyl)oxy]-3-methylbutyl]-penicillin sodium (R)-2-(3-isoxazolylcarbonyloxy)-isocaproic acid was prepared via its benzyl ester in a manner analogous to that described for the preparation of the starting material in Example 1.

In a manner analogous to that described in Example 1, utilizing the above (R)-2-(3-isoxazolylcarbonyloxy)-isocaproic acid there was obtained [(R)-1-[(3-isoxazolylcarbonyl)oxy]-3-methylbutyl]penicillin sodium; mp 188° (with decomposition); $[\alpha]_D^{25} = +209.6°$ (c = 1 in ethanol).

EXAMPLE 28

[(R)-1-[(3-indolylcarbonyl)oxy]-3-methylbutyl]-penicillin sodium

The (R)-2-(3-indolylcarbonyloxy)-isocaproic acid was prepared via its benzyl ester in a manner analogous to that described for the preparation of the starting material in Example 1.

In a manner analogous of that described in Example 1, utilizing as a starting material (R)-2-(3-isoxazolylcarbonyloxy)-isocaproic acid there was obtained. [(R)-

1-[(3-isoxazolylcarbonyl)-oxy]-3-methylbutyl]penicillin sodium; mp 188° (with decomposition); $[\alpha]_D^{25} = +209.6°$ (c = 1 in ethanol).

EXAMPLE 29

[(S)-1-(isonicotinoyloxy)-3-methylbutyl]-penicillin sodium (S)-2-(isonicotinoyloxy)-isocaproic acid; [mp 138°–139°; $[\alpha]_D^{25} = 22.3°$ (c = 2 in ethanol)] was prepared via its benzyl ester in a manner analogous to that described for the preparation of the starting material in Example 1. The resulting compound was then treated with thionyl chloride to yield (S)-2-(isonicotinoyloxy)-isocaproic acid hydrochloride.

In a manner analogous to that described in Example 2, utilizing the thus-formed (S)-2-isonicotinoyloxy)-isocaproic acid hydrochloride there was obtained [(S)-1-(isonicotinoyloxy)-3-methylbutyl]-penicillin sodium; mp. 177° (with decomposition); $[\alpha]_D^{25} = +225°$ (c = 2 in water).

EXAMPLE 30

[(RS)-1-[(2,6-dimethylisonicotinoyl)oxy]-3-methylbutyl]penicillin sodium (RS)-2-(2,6-dimethylisonicotinoyloxy)-isocaproic acid (mp. 95°–96°) was prepared via its benzyl ester in a manner analogous to that described for the preparation of the starting material in Example 35. The resulting compound was treated with thionyl chloride to yield (RS)-2-(2,6-dimethylisonicotinoyloxy)-isocaproic acid hydrochloride.

In a manner analogous to that described in Example 2, utilizing the above (RS)-2-(2,6-dimethylisonicotinoyloxy)-isocaproic acid hydrochloride there was obtained [(RS)-1-[(2,6-dimethylisonicotinoyl)oxy]-3-methylbutyl]penicillin sodium; $[\alpha]_D^{25} = +159°$ (c = 2 in water).

EXAMPLE 31

[(R)-1-cinchoninoyloxy)-3-methylbutyl]penicillin sodium (R)-2-(cinchoninoyloxy)-isocaproic acid was prepared via its benzyl ester in a manner analogous to that described for the preparation of the starting material in Example 1.

In a manner analogous to that described in Example 1, utilizing the thus-formed (R)-2-(cinchoninoyloxy)-isocaproic acid there was obtained [(R)-1-cinchoninoyloxy)-3-methylbutyl]penicillin sodium; mp 143° (with decomposition); $[\alpha]_D^{25} = +208.7°$ (c = 1 in ethanol).

EXAMPLE 32

[(R)-1-[(7-chlorocinchoninoyl)oxy]-3-methylbutyl]-penicillin sodium (R)-2-(7-chlorocinchoninoyloxy)-isocaproic acid was prepared via its benzyl ester in a manner analogous to that described for the preparation of the starting material in Example 1.

In a manner analogous to that described in Example 1, utilizing as a starting material (R)-2-(7-chlorocinchoninoyloxy)-isocaproic acid there was obtained [(R)-1-[(7-chlorocinchoninoyl)oxy]-3methylbutyl]-penicillin sodium; mp 135° (with decomposition); $[\alpha]_D^{25} = +196.4°$ (c = 1 in ethanol).

EXAMPLE 33

[(R)-1-[(2-chloronicotinoyl)-oxyl]-3-methylbutyl]-penicillin potassium (R)-2-(2-chloronicotinoyloxy)-isocaproic acid; mp 64°–67°; $[\alpha]_D^{25} = +17.5°$ (c = 1 in methanol) was prepared via tert. butyl ester in a manner analogous to that described for the preparation of the starting material in Example 16.

In a manner analogous to that described in Example 1, utilizing the above (R)-2-(2-chloronicotinoyloxy)-isocaproic acid there was obtained [(R)-1-[(2-chloronicotinoyl)oxy]-3-methylbutyl]penicillin potassium; mp 120° (with decomposition); $[\alpha]_D^{25} = +167.3°$ (c = 1 in water).

EXAMPLE 34

[(R)-3-methyl-1-(quinaldoyloxy)-butyl]penicillin sodium (R)-2-(quinaldoyloxy)-isocaproic acid was prepared via its benzyl ester in a manner analogous to that described for the preparation of the starting material in Example 22.

In a manner analogous to that described in Example 1, utilizing the thus-formed (R)-2-(quinaldoyloxy)-isocaproic acid there was obtained [(R)-3-methyl-1-(quinaldoyloxy)-butyl]penicillin sodium; mp 170° (with decomposition); $[\alpha]_D^{25} = +119.3°$ (c = 1 in ethanol).

EXAMPLE 35

[(RS)-1-(isonicotinoyloxy)-3-methylbutyl]penicillin sodium

A total of 29.5 g of benzyl-(RS)-α-bromo-isocaproate was added dropwise at 60° with stirring over a period of 15 minutes to a solution of 12.8 g of isonicotinic acid in a mixture of 60 ml. of dimethyl-formamide and 14.8 ml of triethylamine. The reaction mixture was stirred for 5 hours at 90°. The triethylamine hydrobromide was then filtered off by suction and the filtrate evaporated under reduced pressure at 60°. The residue was dissolved in 100 ml of ethyl acetate and filtered and the filtrate washed three times with 15 ml portions of 1-N potassium bicarbonate solution and twice with 20 ml portions of water. The ethyl acetate solution was dried with magnesium sulphate and evaporated under reduced pressure at 45°. Benzyl-(RS)-2-(isonicotinoyloxy)-isocaproate was obtained as an oil.

For purification, the ester formed above was dissolved in 10 ml of ethyl acetate and the resulting solution mixed with a solution of 19 g of p-toluenesulphonic acid in 35 ml. of ethyl acetate and crystallized for 2 hous at 0°. The resulting benzyl-(RS)-2-(isonicotinoyloxy)-isocaproate p-toluene-sulphonate was filtered off by suction, washed with 100 ml of ether and dried under reduced pressure at 60° to give a compound of melting point 136°. The p-toluenesulphonate was dissolved in 30 ml of water, the solution adjusted to pH 9 with potassium carbonate and extracted twice with 50 ml portions of ethyl acetate. The ethyl acetate solution was washed twice with 10 ml portions of water, dried with magnesium sulphate and evaporated under reduced pressure at 40°. Crystallization of the resulting oil from low-boiling petroleum ether gave benzyl-(RS)-2-(isonicotinoyloxy)-isocaproate; mp 49°–50°.

8.2 g of benzyl-(RS)-2-(isonicotinoyloxy)-isocaproate were hydrogenated in 50 ml of alcohol after the addition of 800 mg. of palladium-on-charcoal (5 percent) until the theoretical amount of hydrogen had been taken up. The catalyst was then filtered off and the filtrate evaporated under reduced pressure at 45°. The resulting oil was dissolved in excess sodium bicarbonate solution and extracted twice with 20 ml portions of ether and the bicarbonate solution adjusted to pH 2.5 with 3-N hydrochloric acid. The acidic solution was extracted twice with 70 ml portions of ethyl acetate. After being washed twice with 20 ml portions of 5 percent sodium chloride solution, the ethyl acetate solution was dried with magnesium sulphate and evaporated under reduced pressure at 45°. The resulting oil was crystallized from ether/-petroleum ether to yield (RS)-2-(isonicotinoyloxy)-isocaproic acid; mp 98°–100°.

In a manner analogous to that described in Example 1, utilizing as a starting material (RS)-2-(isonicotinoyloxy)-isocaproic acid there was obtained [(RS)-1-(isonicotinoyloxy)-3-methylbutyl]penicillin sodium; $[\alpha]_D^{25} = +197.5°$ (c = 2 in water).

EXAMPLE 36

[(RS)-1-(isonicotinoyloxy)butyl]penicillin sodium

The (RS)-2-(isonicotinoyloxy)-valeric acid, melting point 152°–153° was prepared via its benzyl ester in a manner analogous to that described for the preparation of the starting material in Example 35.

In a manner analogous to that described in Example 2, utilizing as a starting material (RS)-2-(isonicotinoyloxy)-valeric acid there was obtained [(RS)-1-(isonicotinoyloxy)-butyl]penicillin sodium; $[\alpha]_D^{25} = +222°$ (c = 2 in water).

EXAMPLE 37

[(R)-1-(nicotinoyloxy)-3-methylbutyl]penicillin potassium (R)-2-(nicotinoyloxy)-isocaproic acid was prepared via its benzyl ester in a manner analogous to that described for the preparation of the starting material in Example 22.

In a manner analogous to that described in Example 1, utilizing as a starting material (R)-2-(nicotinoyloxy)-isocaproic acid there was obtained [(R)-1-(nicotinoyloxy)-3-methylbutyl]penicillin potassium; mp 195° (with decomposition); $[\alpha]_D^{25} = +210.4°$ (c = 1 in water).

EXAMPLE 38

[(R)-3-methyl-1-(2-thenoyloxy)butyl]penicillin sodium

The (R)-2-(2-thenoyloxy)-isocaproic acid $[\alpha]_D^{25} = +13.7°$ (c = 2 in ethanol) was prepared via its tert. butyl ester in a manner analogous to that described for the preparation of the starting material in Example 16.

In a manner analogous to that described in Example 1, utilizing the above (R)-2-(2-thenoyloxy)-isocaproic acid there was obtained [(R)-3-methyl-1-(2-thenoyloxy)butyl]penicillin sodium; $[\alpha]_D^{25} = +103°$ (c = 1 in water).

EXAMPLE 39

[3-methyl-1-[(pyrrol-2-ylcarbonyl)-oxy]butyl]penicillin sodium 2-(2-pyrrolylcarbonyloxy)-isocaproic acid was prepared via its benzyl ester in a manner analogous to that described for the preparation of the starting material in Example 35.

In a manner analogous to that described in Example 3, utilizing the above 2-(2-pyrrolylcarbonyloxy)-isocaproic acid there was obtained [3-methyl-1-[(pyrrol-2-ylcarbonyl)oxy]butyl]penicillin sodium as a diastereomeric mixture; mp 208° (with decomposition); $[\alpha]_D^{25} = +187.5°$ (c = 1 ethanol).

EXAMPLE 40

[3-methyl-1-[(1-oxido-isonicotinoyl)oxy]butyl]-penicillin sodium (R)-2-(1-oxido-isonicotinoyloxy)-isocaproic acid, mp 168°–169° $[\alpha]_D^{25} = +4.2°$ (c = 2 in ethanol) was prepared via its benzyl ester in a manner analogous to that described for the preparation of the starting material in Example 22.

In a manner analogous to that described in Example 1, utilizing the thus-formed (R)-2-(1-oxido-isonicotinoyloxy)-isocaproic acid there was obtained [3-methyl-1-[(1-oxidoisonicotinoyl)oxy]butyl]penicillin sodium; mp 195° (with decomposition); $[\alpha]_D^{25} = +187°$ (c = 2 in water).

EXAMPLE 41

[(R)-1-[(2,4-dimethyl-5-pyrimidinylcarbonyl)oxy]-3-methylbutyl]penicillin sodium (R)-2-(2,4-dimethyl-5-pyrimidinylcarbonyloxy)-isocaproic acid, an oily substance, was prepared via its benzyl ester in a manner analogous to that described for the preparation of the starting material in Example 1.

In a manner analogous to that described in Example 3, utilizing as a starting material (R)-2-(2,4-dimethyl-5-pyrimidinylcarbonyloxy)-isocaproic acid there was obtained [(R)-1-[(2,4-dimethyl-5-pyrimidinylcarbonyl)oxy]-3-methylbutyl]penicillin sodium, mp 185° (with decomposition); $[\alpha]_D^{25} = +225°$ (c = 1 in water).

EXAMPLE 42

[(R)-1-[(5-pyrimidinylcarbonyl)oxy]-3-methylbutyl]-penicillin sodium (R)-2-(5-pyrimidinylcarbonyloxy)-isocaproic acid, an oily substance, was prepared via its benzyl ester in a manner analogous to that described for the preparation of the starting material in Example 1.

In a manner analogous to that described in Example 3, utilizing the thus-formed (R)-2-(5-pyrimidinylcarbonyloxy)-isocaproic acid there was obtained [(R)-1[(5-pyrimidinylcarbonyl)oxy-3-methylbutyl]penicillin sodium; mp 205° (with decomposition); $[\alpha]_D^{25} = +237°$ (c = 1 in ethanol).

EXAMPLE 43

[(R)-1-(2-methoxycarbonylnicotinoyloxy)-3-methylbutyl]penicillin sodium (R)-2-(2-methoxycarbonyl-nicotinoyloxy)-isocaproic acid; mp. 63°–65°; $[\alpha]_D^{25} = 27.1°$ (c = 1 in methanol) prepared via its benzyl ester in a manner analogous to that described for the preparation of the starting material in Example 3.

In a manner analogous to that described in Example 3, utilizing the above (R)-2-(2-methoxycarbonyl-nicotinoyloxy)-isocaproic acid there was obtained [(R)-1-(2-methoxycarbonyl-nicotinoyloxy)-3-methylbutyl]penicillin sodium which melts above 145° (with decomposition); $[\alpha]_D^{25} = +195°$ (c = 1 in water).

EXAMPLE 44

[(R)-1-(5-methoxymethyl-2-furoyloxy)-3-methylbutyl]penicillin sodium (R)-2-(5-methoxymethyl-2-furoyloxy)-isocaproic acid (melting point 73°–74°) was prepared via its benzyl ester in a manner analogous to that described for that preparation of the starting material in Example 1.

In a manner analogous to that described in Example 1, utilizing as a starting material (R)-2-(5-methoxymethyl-2-furoyloxy)-isocaproic acid there was obtained [(R)-1-(5-methoxymethyl-2-furoyloxy)-3-methylbutyl]penicillin sodium; mp 173° (with decomposition); $[\alpha]_D^{25} = +203°$ (c = 1 in water).

EXAMPLE 45

[(R)-3-methyl-1-[(S)-5-oxotetrahydro-2-furoyloxy]-butyl]penicillin sodium (R)-2-[(S)-5-oxotetrahydro-2-furoyloxy]-isocaproic acid; mp 115°–116°; $[\alpha]_D^{25} = +23.4°$ (c = 0.5 in dioxan) was prepared via its benzyl ester in a manner analogous to that described for the preparation of the starting material in Example 22.

In a manner analogous to that described in Example 1, utilizing as a starting material (R)-2-[(S)-5-oxotetrahydro-2-furoyloxy]-isocaproic acid there was obtained [(R)-3-methyl-1-[(S)-5-oxotetrahydro-2-furoyloxy]butyl]penicillin sodium, mp 216° (with decomposition); $[\alpha]_D^{25} = +235°$ (c = 1 in water).

EXAMPLE 46

[(R)-3-methyl-1-[(R)-5-oxotetrahydro-2-furoyloxy]-butyl]penicillin sodium (R)-2[(R)-5-oxotetrahydro-2-furoyloxy]-isocaproic acid, an oily substance, prepared via its benzyl ester in a manner analogous to that described for the preparation of the starting material in Example 22.

In a manner analogous to that described in Example 1, utilizing the thus-formed (R)-2-[(R)-5-oxotetrahydro-2-furoyloxy]-isocaproic acid there was obtained [(R)-3-methyl-1-[(R)-5-oxotetrahydro-2-furoyloxy]-butyl]penicillin sodium; mp 215° (with decomposition; $[\alpha]_{D25} = +196°$ (c = 1 in water).

EXAMPLE 47

The following composition was prepared as follows and filled into gelatin capsules.

| Ingredient | Amount per Capsule |
|---|---|
| [(R)-1-(2-furoyloxy)-3-methylbutyl] penicillin sodium | 526 mg. |
| LUVISKOL K 90 (I) | 23 mg. |
| Mannkol | 20 mg. |
| Talc | 19 mg. |
| Magnesium stearate | 2 mg. |
| Total | 600 mg. |

The penicillin was homogeneously blended with the LUVISKOL and mannitol and compressed into slugs. The slugs were then passed through a suitable sieving machine and, after blending with the tack and magnesium stearate, filled into suitable gelatin capsules.

EXAMPLE 48

Reconstitutable injectable preparations were prepared by lyophilizing and hermetically sealing ampoules each containing 2 ml. of a sterile solution containing 263 mg. of [(R)-1-(2-furoyloxy)-3-methylbutyl]penicillin sodium, 1.1 mg. of methyl-p-hydroxybenzoate and 0.135 mg. of propyl-p-hydroxybenzoate.

We claim:

1. A compound of the formula

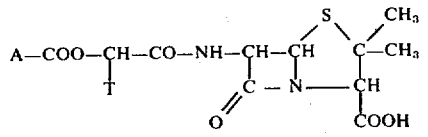

wherein A is selected from the group consisting of furyl, tetrahydrofuryl and thienyl, and T is selected from the group consisting of $C_2$–$C_5$ *alkyl*, $C_2$–$C_5$ alkenyl, cyclopropylmethyl, cyclobutylmethyl and cyclopentyl and pharmaceutically acceptable salts and hydrated forms thereof.

2. A compound selected from the group consisting of (R)-1-(2-furoyloxy)-3-methylbutyl-penicillin and pharmaceutically acceptable salts and hydrated forms thereof.

* * * * *